US008686021B2

(12) United States Patent
Polenzani et al.

(10) Patent No.: US 8,686,021 B2
(45) Date of Patent: Apr. 1, 2014

(54) USE OF A BENZOYL DERIVATIVE OF 3-AMINOCARBAZOLE FOR THE TREATMENT OF A DISORDER ASSOCIATED WITH THE PRODUCTION OF PROSTAGLANDIN $E_2$ ($PGE_2$)

(75) Inventors: Lorenzo Polenzani, Grottaferrata (IT); Giorgina Mangano, Rome (IT); Isabella Coletta, Rome (IT); Maria Alessandra Alisi, Rome (IT); Nicola Cazzolla, Albano Laziale (IT); Guido Furlotti, Rome (IT); Caterina Maugeri, Rome (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 1169 days.

(21) Appl. No.: 11/909,393

(22) PCT Filed: May 3, 2006

(86) PCT No.: PCT/EP2006/004348

§ 371 (c)(1),
(2), (4) Date: Jun. 13, 2008

(87) PCT Pub. No.: WO2006/122680

PCT Pub. Date: Nov. 23, 2006

(65) Prior Publication Data

US 2008/0287518 A1    Nov. 20, 2008

(30) Foreign Application Priority Data

May 19, 2005   (IT) .............................. MI2005A0909

(51) Int. Cl.
*A61K 31/404*   (2006.01)
*A61P 35/00*    (2006.01)

(52) U.S. Cl.
USPC ........... 514/411; 514/322; 514/318; 514/415; 514/230.2; 514/232.8; 514/320; 514/321; 514/339; 546/199; 546/229; 546/194; 546/277.4; 546/84; 548/362.1; 548/362.5; 548/444; 548/452; 548/511

(58) Field of Classification Search
USPC ........... 514/411, 322, 318, 415, 230.2, 232.8, 514/320, 321, 339; 546/199, 229, 194, 546/277.4, 84; 548/362.1, 362.5, 444, 452, 548/511
See application file for complete search history.

(56) References Cited

U.S. PATENT DOCUMENTS 6,399,631 B1    6/2002   Elliott et al.

FOREIGN PATENT DOCUMENTS

WO   WO 01/07409 A1    2/2001
WO   WO 02/096902 A1   12/2002

OTHER PUBLICATIONS

Jkimball document, 2003, retrieved from the internet on Jul. 20, 2010, URL: http://web.archive.org/web/20031204214536/http://users.rcn.com/jkimball.ma.ultranet/BiologyPages/I/Inflammation.html.*
Wellen et al (The Journal of clinical investigation, 2003, vol. 112 (12), pp. 1785-1788).*
Conway et al. (Obesity reviews, 2004, vol. 5(3), pp. 145-151).*
U.S. Appl. No. 11/916,487, filed Dec. 4, 2007, Alisi, et al.
Hiroyasu Inoue, et al., "Feedback Control of Cyclooxygenase-2 Expression Through PPARγ", Journal of Biological Chemistry, vol. 275, No. 36, Sep. 8, 2000, pp. 28028-28032.
Joseph P. Portanova, et al., "Selective Neutralization of Prostaglandin E2 Blocks Inflammation, Hyperalgesia, and Interleukin 6, Production In Vivo", J. Exp. Med., vol. 184, No. 3, 1996, pp. 883-891.
Akinori Ueno, et al., "Major Roles of Prostanoid Receptors IP and EP$_3$ in Endotoxin-Induced Enhancement of Pain Perception", Biochemical Pharmacology, vol. 62, No. 2, 2001, pp. 157-160.
Fumitaka Ushikubi, et al., "Impaired Febrile Response in Mice Lacking the Prostaglandin E Receptor Subtype EP3", Nature, vol. 395, Sep. 17, 1998, pp. 281-284.
Garret A. Fitzgerald, et al., "The Coxibs, Selective Inhibitors of Cyclooxygenase-2", N. Engl. J. Med. vol. 345, No. 6, Aug. 9, 2001, pp. 433-442.
Samir Malhotra, et al., "COX-2 Inhibitors: A Class Act or Just Vigorously Promoted", Medscape General Medicine, vol. 6, No. 1, 2004, pp. 1-5.
Debabrata Mukherjee, et al., "Cardiovascular Risk and COX-2 Inhibitors", Arthritis Research and Therapy, vol. 5, No. 1, 2003, pp. 8-11.
U.S. Appl. No. 12/914,551, filed Oct. 28, 2010, Alisi, et al.

* cited by examiner

*Primary Examiner* — Savitha Rao
(74) *Attorney, Agent, or Firm* — Oblon, Spivak, McClelland, Maier & Neustadt, L.L.P.

(57) ABSTRACT

Use of a benzoyl derivative of 3-aminocarbazole to produce a drug for the preventive or therapeutic treatment of a disorder selected form the group comprising inflammatory processes, pain, fever, tumors, Alzheimer's disease and atherosclerosis. Method for the preventive or therapeutic treatment of a disorder selected from the group comprising inflammatory processes, pain, fever, tumors, Alzheimer's disease and atherosclerosis in which a therapeutically effective quantity of a benzoyl derivative of 3-aminocarbazole according to the invention is administered to an individual.

11 Claims, No Drawings

USE OF A BENZOYL DERIVATIVE OF 3-AMINOCARBAZOLE FOR THE TREATMENT OF A DISORDER ASSOCIATED WITH THE PRODUCTION OF PROSTAGLANDIN E$_2$ (PGE$_2$)

FIELD OF THE INVENTION

This invention relates to the use of a benzoyl derivative of 3-aminocarbazole in Table 1 below for the production of a pharmaceutical which is useful in the treatment of disorders associated with the production of prostaglandin E$_2$ (PGE$_2$) such as, for example, inflammatory processes, pain, fever, tumours, Alzheimer's disease and atherosclerosis.

STATE OF THE ART

Interest in prostaglandins E$_2$ (PGE$_2$) arises from their role as bioregulators, together with other prostanoids produced by the arachidonic acid metabolic route, and as mediators of inflammation.

As is known, prostanoids are a class of compounds which include prostaglandins, thromboxanes and prostacyclins. Prostanoids are lipid mediators which act as local hormones on the cells adjacent to the site of their release. Prostanoids are mainly produced from arachidonic acid through cycloxygenase-activated enzyme oxidation. Cycloxygenases (prostaglandin G/H synthases) catalyse the sequential formation of PGG$_2$ and PGH$_2$ from arachidonic acid. PGH$_2$ is then converted into the various prostanoids through specific enzymes. Prostaglandins D$_2$ (PGD$_2$), prostaglandins E$_2$ (PGE$_2$), prostaglandins F$_{2\alpha}$ (PGF$_{2\alpha}$), prostaglandins I$_2$ (PGI$_2$) and thromboxanes A$_2$ (TXA$_2$) are formed in this way.

Prostanoids do not accumulate, except in seminal fluid. Following various stimuli (inflammatory, immunological, hormonal stimuli, ultraviolet light, tumoural agents and also mechanical agitation) they are synthesized and released into the extracellular space, from which they pass into the plasma, urine and other biological fluids.

Prostanoids play an important part in the mechanisms defending organ function and the integrity of the body. This is demonstrated by their cytoprotective function in the gastrointestinal tract, their regulation of kidney function and microcirculation, their regulation of platelet aggregation and blood coagulation, their involvement in the differentiation of immune cells and the repair of wounds, and in bone metabolism and ovulation.

In particular the vasoprotective action of PGI$_2$, which is essential for maintaining vascular tone and for preventing thromboembolism and atherosclerosis at endothelial level and the anti-inflammatory and anti-proliferative action of PGD$_2$, whose metabolite, 15d-PGJ$_2$, is capable of exerting anti-inflammatory effects through the activation of nuclear PPAR$_\gamma$ (peroxisome proliferator-activated receptor-gamma) receptors must be emphasized (Inoue et al., "Feedback control of cyclooxygenase-2 expression through PPARgamma", J. Biol. Chem. 2000, 275 (36): 28028-28032).

Prostanoids are therefore bioregulators, but they are also important mediators of inflammation and other diseases.

In particular PGE$_2$ are abundant at inflammation sites and are responsible for the various pathological aspects of acute and chronic inflammation such as oedema, the formation of erythema, inflammatory pain, inflammation of the joints and fever. PGE$_2$ are in fact powerful proinflammatory agents and algogens. Anti-PGE$_2$ antibodies have anti-inflammatory activity and animals devoid of receptors for PGE$_2$ demonstrate a reduced response to inflammatory stimuli (Portanova et al., "Selective neutralization of prostaglandin E2 blocks inflammation, hyperalgesia, and interleukin 6 production in vivo", J. Exp. Med. 1996, 184(3):883; Ueno et al., "Major roles of prostanoid receptors IP and EP (3) in endotoxin-induced enhancement of pain perception", Biochem. Pharmacol. 2001, 62(2):157-160) and an absence of febrile response to pyrogenic stimuli (Ushikubi et al., "Impaired febrile response in mice lacking the prostaglandin E receptor subtype EP3", Nature 1998, 395:281-284). Because of their inhibitory action on cycloxygenases 1 and 2 (FitzGerald and Patrono, "The coxibs, selective inhibitors of cyclooxygenase-2", N. Engl. J. Med. 2001, 345(6):433-442) the non-steroid anti-inflammatory (NSAI) drugs and COX-2-selective drugs currently in use reduce the symptoms associated with inflammation through non-selective inhibition of the production of eicosanoids (PGE$_2$, PGD$_2$, PGF$_{2\alpha}$, PGI$_2$ and TXA$_2$).

In particular the COX-2 selective drugs currently available on the market have reduced gastrointestinal toxicity in comparison with conventional non-steroid anti-inflammatory (NSAI) drugs. However these COX-2 selective drugs reduce the production of vascular prostacyclin (PGI$_2$, which is mainly produced from COX-2), altering the normal equilibrium between prothrombotic and antithrombotic eicosanoids in favour of the prothrombotic ones (TXA$_2$, which is mainly produced from COX-1), and give rise to an increased risk of thrombotic-cardiovascular events (S. Malhotra, MD, DM; N. Shafiq, MD; P. Pandhi, MD, Medscape General Medicine 6(1), 2004; D. Mukherjee and E. J. Topol, Cardiovascular risk and COX-2 inhibitors, Arthritis Res. Ther. 2003, 5:8-11-2002).

Patent applications WO 01/07409 A1 and WO 02/096902 A1 relate to numerous carbazole derivatives represented by an extensive general formula comprising the base group of 3-aminocarbazole substituted in any position, including the nitrogen atom, with one or more aliphatic and/or aromatic organic groups or residues. According to these documents the aforesaid carbazole derivatives are capable of selectively binding to the human Y5 receptor and modulating its activity. As a consequence of this, these carbazole derivatives are therefore likely to be useful in the treatment of hunger and metabolic disorders such as obesity, bulimia nervosa, anorexia nervosa, sleep disorders, morphine dependence and epileptic attacks.

SUMMARY OF THE INVENTION

It has now surprisingly been found that some benzole derivatives of 3-aminocarbazole are capable of selectively inhibiting the production of prostaglandin E$_2$ (PGE$_2$).

The useful compounds according to this invention are capable of reducing the production of PGE$_2$ and are therefore active in all pathological conditions where PGE$_2$ acts as a mediator (for example, pain, fever and inflammatory response).

The useful compounds according to this invention inhibit PGE$_2$ synthesis selectively. The selective inhibition of PGE$_2$ has the advantage of inhibiting a powerful mediator of inflammation, pain and fever, leaving the production of the other prostanoids which are produced in cascade from arachidonic acid at the same time, such as PGF$_{2\alpha}$, TXA$_2$, PGI$_2$ and PGD$_2$, unchanged. All the mechanisms for the defense of organ functions and the integrity of the body which are typical of the activities of the other prostanoids therefore remain unaffected.

In a similar way to conventional non-steroid anti-inflammatories the useful compounds according to this invention have anti-inflammatory, antipyretic and analgesic properties, and are therefore active in diseases such as inflammation, pain, fever, rheumatoid arthritis and arthrosis disease. In addition to this, given that the effects of PGE$_2$ on tumours, Alzheimer's disease and atherosclerosis are known in the literature, the useful compounds according to this invention are also likely to find application in the prevention and treatment of these diseases.

Advantageously the useful compounds according to this invention nevertheless have less adverse effects in comparison with NSAI and COX-2 selective drugs which in inhibiting cycloxygenases do not discriminate between the various prostanoids. In particular the useful compounds according to this invention have reduced gastrointestinal, renal and vascular toxicity.

DETAILED DESCRIPTION OF THE INVENTION

In a first aspect this invention therefore relates to the use of a compound selected from the group comprising the benzoyl derivatives of 3-aminocarbazole in Table 1 below for the production of a drug for the preventive or therapeutic treatment of a disorder selected from the group comprising inflammatory processes, pain, fever, tumours, Alzheimer's disease and atherosclerosis.

In addition to this, in a second aspect, this invention relates to a method for the preventive or therapeutic treatment of a disorder selected from the group comprising inflammatory processes, pain, fever, tumours, Alzheimer's disease and atherosclerosis, in which a therapeutically effective quantity of a compound selected from the group comprising the benzoyl derivatives of 3-aminocarbazole in Table 1 below is administered to an individual.

Typical examples of inflammatory processes which might derive benefit from this invention are: oedema, erythema, inflammation of the joints, rheumatoid arthritis, arthrosis disease and the like.

Typical examples of tumours which may benefit from this invention are carcinomas and adenocarcinomas of the colon-rectum and lungs.

Typically the benzoyl derivatives of 3-aminocarbazole according to this invention are administered to a mammal. Preferably they are administered to man.

The useful compound according to this invention is selected from the group comprising the benzoyl derivatives of 3-aminocarbazole of formula (I) indicated in Table 1 below:

TABLE 1

(I)

| Compound | $R_1$ | $R_2$ | $R_3$ | $R_4$ | $R_5$ |
|---|---|---|---|---|---|
| 1 | Cl | H | H | H | H |
| 2 | $CH_3$ | H | H | H | H |
| 3 | Br | H | H | H | H |
| 4 | I | H | H | H | H |
| 5 | $NO_2$ | H | H | H | H |
| 6 | Cl | H | H | H | Cl |
| 7 | Cl | H | H | $NO_2$ | H |
| 8 | Cl | H | H | Cl | H |

The useful compounds according to this invention may be prepared according to methods known in the literature, for example as described in patent application WO 02/096902 A1.

Preferably the drug according to this invention is prepared in the form of suitable dosing forms.

Examples of suitable dosing forms are tablets, capsules, coated tablets, granules, solutions and syrups for oral administration, creams, unguents and medicated plasters for topical administration, suppositories for rectal administration, and sterile solutions for administration by injection, aerosol or ophthalmic means.

Advantageously these dosing forms are formulated in such a way as to ensure controlled release of a compound in Table 1 over time. In fact, depending upon the nature of the treatment, the required release time may be very short, normal or protracted.

The dosing forms may also contain other conventional ingredients, such as preservatives, stabilizers, surfactants, buffers, salts to regulate osmotic pressure, emulsifiers, sweeteners, colouring agents, flavourings and the like.

Also, if required by particular treatments, the dosing forms according to this invention may include other pharmacologically active ingredients which it is useful to administer simultaneously.

The quantity of compound according to this invention in the aforesaid dosing forms may vary over a wide range depending upon known factors such as, for example, the type of disorder which has to be treated, the severity of the disorder, the patient's body weight, the dosage form, the administration route chosen, the number of administrations per day and the efficacy of the selected compound. Optimum quantities can however be determined easily in the normal way by those skilled in the art.

Typically the quantity of compound in the dosing forms according to this invention is such as to ensure an administered level of between 0.0001 and 100 mg/kg/day. Even more preferably between 0.01 and 10 mg/kg/day.

The dosing forms of the pharmaceutical composition according to this invention may be prepared using techniques which are well known to pharmaceutical chemists, which include mixing, granulation, compression, dissolution, sterilization and the like.

The following experimental part will illustrate the invention in greater detail, without however in any way restricting it.

Experimental Part

In-Vitro Activity Test

This test is used to evaluate capability to inhibit the production of $PGE_2$ and selectivity with respect to the production of $PGF_2$, for each of the compounds under examination.

Cell line A549, human lung adenocarcinoma, which is particularly sensitive to stimulation with proinflammatory cytokines such as IL-$1_\beta$, and, in response to that stimulation, particularly active in the production and release of two prostanoids: $PGE_2$ and $PGF_{2\alpha}$ (Thoren S., Jakobsson P. J. "Coordinate up- and down-regulation of glutathione-dependent prostaglandin E synthase and cyclooxygenase-2 in A549 cells. Inhibition by NS-398 and leukotriene C4", Eur. J. Biochem. 2000, 267(21):6428-6434)) was used.

The cells were stimulated with IL-$1_\beta$ (1 ng/ml) and at the same time treated with the compounds under test for 18 hours in an appropriate culture medium (DMEM—Dulbecco's Modified Eagles Medium) enriched with 5% bovine foetal serum and L-glutamine (4 mM final) in an incubator at 37° C. and with a $CO_2$ concentration of 5%.

After incubation the quantities of $PGE_2$ and $PGF_{2\alpha}$ produced and released into the supernatant were determined using an EIA kit (manufactured and marketed by Cayman Chemicals, Ann Arbor, Mich., USA).

Indomethacin (Sigma-Aldrich), a non-steroid anti-inflammatory which has demonstrated the same inhibition on both the prostanoids measured, was used as the reference compound.

Compounds A, B and C having the same general formula (I) described above and the substituents indicated in Table 2 were used as comparison compounds. The preparation of these comparison compounds is similar to that of the compounds according to the invention.

TABLE 2

| Compound | $R_1$ | $R_2$ | $R_3$ | $R_4$ | $R_5$ |
|---|---|---|---|---|---|
| A | $OCH_3$ | H | H | H | H |
| B | H | H | H | H | H |
| C | H | H | $CH_3$ | H | H |

The results, shown in Table 3, are expressed as percentage inhibition of the production of $PGE_2$ and $PGF_{2\alpha}$ at a concentration of 10 μm.

TABLE 3

| | % inhibition at 10 μM | |
|---|---|---|
| Compound | $PGE_2$ | $PGF_{2\alpha}$ |
| 1 | 82 | 16 |
| 2 | 83 | 44 |
| 3 | 81 | 0 |
| 4 | 84 | 0 |
| 5 | 27 | 0 |
| 6 | 89 | 51 |
| 7 | 70 | 0 |
| 8 | 93 | 37 |
| A | 98 | 95 |
| B | 46 | 40 |
| C | 43 | 49 |
| Indomethacin | 100 | 100 |

By way of example Table 4 shows $pIC_{50}$ values for some compounds according to the invention where $pIC_{50}$ represents the reciprocal of the logarithm of the $IC_{50}$ which in turn represents the concentration of compound inhibiting 50% of $PGE_2$ or $PGF_2$, production in stimulated cells which were not however treated with that compound.

TABLE 4

| | $pIC_{50}$ | |
|---|---|---|
| Compound | $PGE_2$ | $PGF_{2\alpha}$ |
| 1 | 5.7 | 4.1 |
| 2 | 5.3 | 4.3 |
| 3 | 5.5 | <4 |
| 4 | 5.4 | <4 |
| Indomethacin | 8.3 | 8.6 |

In-Vivo Activity Test

This test makes it possible to evaluate the activity of the compounds according to this invention in a nociceptive test of inflammatory origin. Compound 1 was used for this purpose in an experimental model which provokes pained behaviour induced by acetic acid in mice (Stock, J. L. et al., J. Clin. Inv. 2001, 107:325-331). Female CD-1 mice weighing 25-30 g were used for the test.

The animals were treated orally with compound 1 (30 mg/kg) suspended in methyl cellulose (MTC). The control animals were treated with the vehicle (MTC) alone, orally.

One hour after treatment acetic acid (0.7% v/v in physiological solution, 16 μl/g of body weight) was injected into the animals intraperitoneally to induce inflammatory pain and check the effects of the treatment on the nociceptive response.

The number of stretches, which represents the evaluation parameter for the nociceptive response, was measured immediately after the administration of acetic acid and for the next 20 minutes. The results obtained (mean±SD) are shown in Table 5 below.

TABLE 5

| Compound | No. stretches in 20 min |
|---|---|
| MTC | 58 ± 5 |
| MTC + Compound 1 | 40 ± 5 |

Test on Human Primary Endothelial Cells (HUVEC)

This test is used to evaluate the ability of the compounds in Table 2 to inhibit the production of $PGI_2$.

The absence of inhibitory activity on these prostanoids may ensure that the vasoprotective action of $PGI_2$ is maintained and provides useful pharmacological information about the absence of adverse effects on the endothelium.

Compound 1 was used in the test.

The action of the compound under test was evaluated in HUVEC cells under basal and stimulation conditions (J. Immunol. 1989 Jun. 1; 142(11):3993-9).

The results are shown in Table 6 and are expressed as percentage inhibition in comparison with control enzyme activity.

Indomethacin was used as the reference compound.

TABLE 6

| Compound (10 μM) | Test for the secretion of $PGI_2$ | % inhibition |
|---|---|---|
| 1 | Basal (HUVEC) | 0 |
| 1 | Stimulated (HUVEC) | 0 |
| Indomethacin | Stimulated (HUVEC) | 100 |

The invention claimed is:

1. A method for treating a disorder selected from the group consisting of an inflammatory process or pain, wherein the inflammatory process is selected from the group consisting of oedema, erythema, inflammation of the joints, rheumatoid arthritis and arthrosis disease in which a therapeutically effective quantity of a compound selected from the group comprising the benzoyl derivatives of 3-amino carbazole of formula (I) indicated in Table 1 below

TABLE 1

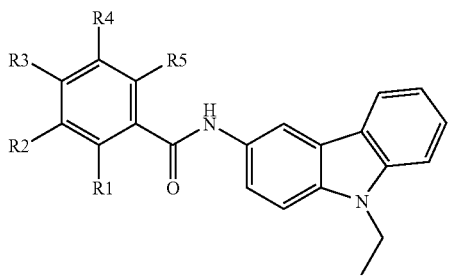

(I)

is administered to an individual

| Compound | $R_1$ | $R_2$ | $R_3$ | $R_4$ | $R_5$ |
|---|---|---|---|---|---|
| 1 | Cl | H | H | H | H |
| 2 | $CH_3$ | H | H | H | H |
| 3 | Br | H | H | H | H |
| 4 | I | H | H | H | H |
| 5 | $NO_2$ | H | H | H | H |
| 6 | Cl | H | H | H | Cl |
| 7 | Cl | H | H | $NO_2$ | H |
| 8 | Cl | H | H | Cl | H. |

2. The method of claim 1, wherein the compound is administered in the amount of from 0.0001 to 100 mg/kg/day.

3. The method of claim 1, wherein the compound is administered in the amount of from 0.01 to 10 mg/kg/day.

4. The method of claim 1, wherein compound 1 is administered.

5. The method of claim 1, wherein compound 2 is administered.

6. The method of claim 1, wherein compound 3 is administered.

7. The method of claim 1, wherein compound 4 is administered.

8. The method of claim 1, wherein compound 5 is administered.

9. The method of claim 1, wherein compound 6 is administered.

10. The method of claim 1, wherein compound 7 is administered.

11. The method of claim 1, wherein compound 8 is administered.

* * * * *